United States Patent
Abuelhaiga et al.

(10) Patent No.: US 10,413,490 B2
(45) Date of Patent: Sep. 17, 2019

(54) DEODORANT COMPOSITIONS

(71) Applicant: DEAD SEA BROMINE COMPANY LTD., Beer Sheva (IL)

(72) Inventors: Mohammed Abuelhaiga, Kibbutz Mefalsim (IL); Nikolay Fux, Beer Sheva (IL); Ariel Peleg, Lehavim (IL); Meyrav Abecassis Wolfovich, Meitar (IL); Ganit Levi-Ruso, Beer Sheva (IL); Smadar Swissa, Meitar (IL)

(73) Assignee: Dead Sea Bromine Company Ltd., Beer Sheva (IL)

( * ) Notice: Subject to any disclaimer, the term of this patent is extended or adjusted under 35 U.S.C. 154(b) by 0 days.

(21) Appl. No.: 16/064,081

(22) PCT Filed: Nov. 10, 2016

(86) PCT No.: PCT/IL2016/051214
§ 371 (c)(1),
(2) Date: Jun. 20, 2018

(87) PCT Pub. No.: WO2017/115346
PCT Pub. Date: Jul. 6, 2017

(65) Prior Publication Data
US 2019/0000730 A1    Jan. 3, 2019

Related U.S. Application Data

(60) Provisional application No. 62/271,541, filed on Dec. 28, 2015.

(51) Int. Cl.
A61K 8/19 (2006.01)
A61Q 15/00 (2006.01)
C01F 5/14 (2006.01)
C01F 5/24 (2006.01)

(52) U.S. Cl.
CPC ............... *A61K 8/19* (2013.01); *A61Q 15/00* (2013.01); *C01F 5/14* (2013.01); *C01F 5/24* (2013.01); *A61K 2800/30* (2013.01)

(58) Field of Classification Search
None
See application file for complete search history.

(56) References Cited

U.S. PATENT DOCUMENTS

| 4,659,560 A | 4/1987 | Bews et al. |
| 6,605,288 B1 | 8/2003 | Okawa et al. |
| 7,922,991 B2 * | 4/2011 | Mitsuhashi ............ A01N 25/08 162/90 |
| 2005/0129606 A1 | 6/2005 | Mitsuhashi et al. |
| 2008/0207737 A1 | 8/2008 | Zinger |

FOREIGN PATENT DOCUMENTS

RO 101125 B1 * 11/1992 ................ C01F 5/24

OTHER PUBLICATIONS

English language CAS Sci Finder abstract (CAPLUS Acc. No. 1994:248706) of RO 101125 B1 (Nov. 25, 1992).*
International Search Report for PCT/IL2016/051214, dated Feb. 14, 2017; 6 pages.
Written Opinion of the International Searching Authority for PCT/IL2016/051214, dated Feb. 14, 2017; 6 pages.

* cited by examiner

*Primary Examiner* — Brian J Davis
(74) *Attorney, Agent, or Firm* — Roach Brown McCarthy & Gruber, P.C.; Kevin D. McCarthy

(57) ABSTRACT

This invention provides an effective, dermatologically safe composition based on partially carbonated magnesium hydroxide for use in cosmetic formulations.

12 Claims, 8 Drawing Sheets

DEODORANT COMPOSITIONS

FIELD OF THE INVENTION

The present invention relates to a dermatologically safe agent comprising partially carbonated magnesium hydroxide, and further to methods and compositions employing it. Particularly, the invention relates to perspiration-reducing or deodorant formulations.

BACKGROUND OF THE INVENTION

Perspiration is a physiological response to thermal or emotional stimuli during occupational, sporting, or other social events, often resulting in discomforting or even embarrassing experience. Treatments typically include topical deodorants, which usually contain aluminum and zirconium salts. In view of the ever growing number of sensitivities and allergies in the human population, and since still stricter regulations are introduced into cosmetic practice, new antiperspirant and deodorant means are needed on the cosmetic market. For example, US 2008/0207737 related to antiperspirant compositions comprising anti-cholinergic or anti-muscarinic antagonists, but such agents are too invasive for general use. It is therefore an object of the invention to provide a generally applicable and safe perspiration-reducing agent or deodorant. U.S. Pat. No. 6,605,288 relates to deodorant compositions comprising metal salts such as aluminum but also naturally occurring biometals such as calcium, magnesium, and potassium.

It is therefore another object of this invention to provide a perspiration-reducing or deodorant composition containing a naturally occurring biometal, the biometal being magnesium.

It is a further object of the invention to provide a method of manufacturing a perspiration-reducing or deodorant composition, enabling to reduce or obviate the use of aluminum-based agents.

Other objects and advantages of present invention will appear as description proceeds.

SUMMARY OF THE INVENTION

The present invention provides a safe cosmetic formulation comprising, beside cosmetically acceptable solvents and surfactants, a partially carbonated magnesium hydroxide (PCMH) of formula (1):

$$[Mg(OH)_2]_{10-x} \cdot [MgCO_3]_x \cdot [H_2O]_x \quad (1)$$

wherein x is a real number between about 1 and 7. The lower and upper limits correspond to the carbonization extent of about 10% and 70%, respectively. In a preferred embodiment, the invention provides a safe cosmetic perspiration-reducing formulation or a deodorant formulation. The safe cosmetic perspiration-reducing or deodorant formulation according to the invention may comprise PCMH in an amount of from 5 to 30 wt %. Said PCMH for use in cosmetics preferably consists of from about 20 to about 85 wt % magnesium hydroxide, from about 12 to about 65 wt % magnesium carbonate, and from about 2 to about 15 wt % water. In one embodiment of the invention, the perspiration-reducing or deodorant formulation provided by the invention comprises up to 10 wt % aluminum or zirconium salts, such as up to 8 wt %, for example up to 5 wt %. In other embodiment, the invention obviates the use of aluminum or zirconium salts and provides cosmetic perspiration-reducing or deodorant formulations entirely lacking said salts. In a preferred embodiment, the invention is directed to a safe cosmetic perspiration-reducing or deodorant formulation comprising said partially carbonated magnesium hydroxide, solvents, surfactants, bulking agents, and fragrance components, wherein said formulation exhibits antimicrobial activity.

The invention relates to a dermatologically safe agent, essentially consisting of a partially carbonated magnesium hydroxide (PCMH) of formula (1):

$$[Mg(OH)_2]_{10-x} \cdot [MgCO_3]_x \cdot [H_2O]_x \quad (1)$$

wherein x is a real number between about 1 and 7. In an important aspect, the invention relates to a dermatologically safe cosmetically active agent or perspiration-reducing agent.

Said agent, advantageously used in cosmetic perspiration-reducing or deodorant formulations, enables to reduce the use of aluminum-based salts in the formulations, and it even enables to obviate the use of such salts.

The invention relates to a method for reducing the amount of aluminum-based salts in deodorant and perspiration-reducing formulations or for replacing said salts, comprising providing i) cosmetically acceptable magnesium hydroxide and partially reacting it with carbon dioxide, wherein converting between about 10 and 70% of said hydroxide to carbonate, to provide a partially carbonated magnesium hydroxide (PCMH) essentially consisting of magnesium carbonate and water homogeneously dispersed in magnesium hydroxide; ii) mixing said PCMH with cosmetically acceptable solvents and/or surfactants, and optionally with additional components selected from emollients, buffers, bulking agents, thickening agents, moisturizers, fragrance components, and preservatives, thereby obtaining a deodorant or perspiration-reducing formulation free of aluminum and zirconium salts, wherein said PCMH constitutes between 5 and 25 wt % of the formulation; and optionally iii) admixing to said formulation of step ii) up to 10 wt % of aluminum or zirconium salts, such as up to 8 wt % or up to 5 wt %, based on the weight of said formulation.

In one aspect, the invention relates to a method for reducing usual antimicrobial ingredients in cosmetic formulations or for replacing said ingredients, comprising providing i) cosmetically acceptable magnesium hydroxide and partially reacting it with carbon dioxide, wherein converting between about 10 and 70% of said hydroxide to carbonate, to provide a partially carbonated magnesium hydroxide (PCMH) essentially consisting of magnesium carbonate and water homogeneously dispersed in magnesium hydroxide; and ii) mixing said PCMH with cosmetically acceptable solvents and/or surfactants, and optionally with additional components selected from surfactants, emollients, buffers, bulking agents, thickening agents, moisturizers, fragrance components, and preservatives, thereby obtaining a deodorant or perspiration-reducing formulation free of aluminum and zirconium salts, wherein said PCMH constitutes between 5 and 25 wt % of the formulation. In one embodiment, the invention relates to a method for eliminating usually employed commercial antimicrobial ingredients in deodorant formulations or perspiration-reducing formulations.

The invention provides a method of manufacturing a cosmetic perspiration-reducing or deodorant formulation comprising steps of i) providing cosmetically acceptable magnesium hydroxide and partially reacting it with carbon dioxide, the extent of carbonation, or shortly carbonation, being from about 5% to 75%, preferably from about 10% to about 70%, to provide PCMH essentially consisting of magnesium carbonate and water homogeneously dispersed in magnesium hydroxide; ii) mixing said PCMH with cosmetically acceptable solvents and/or surfactants; and optionally iii) mixing with additional components selected from emollients, buffers, bulking agents, thickening agents, moisturizers, fragrance components, propellants, and preservatives; thereby obtaining a safe perspiration-reducing or deodorant formulation, free of aluminum and zirconium salts.

Said PCMH is formed according to the following reaction:

wherein x is a real number between about 1 and 7. The method, in one embodiment of the invention, comprises steps of i) preparing an aqueous 10-40% slurry of magnesium hydroxide in a reactor; ii) heating the slurry to 30-80° C. and stirring; iii) injecting to the bottom of the reactor carbon dioxide for the time needed to the desired carbonation; iv) removing the partially carbonated magnesium hydroxide from the slurry and drying it to a moisture level of less than 2%, when measured as loss of drying at 105° C. for 60 minutes. In one preferred embodiment, said cosmetically acceptable magnesium hydroxide is a product of Dead Sea Periclase (DSP), Israel.

The invention aims at providing safe agents to be used in the preparation of cosmetic formulations for reducing perspiration and the resulting malodor, which agents being easily obtained and being generally acknowledged as safe. Partially carbonated magnesium hydroxide compositions provided by the invention advantageously serve as deodorant agents in cosmetic formulations.

BRIEF DESCRIPTION OF THE DRAWINGS

The above and other characteristics and advantages of the invention will be more readily apparent through the following examples, and with reference to the appended drawings, wherein FIG. 1. shows the bulk density measurements for partially carbonized magnesium hydroxide (PCMH) in accordance with the invention (diamonds) and for comparative mixtures of magnesium hydroxide and carbonate (squares).

DETAILED DESCRIPTION OF THE INVENTION

It has now been found that partially carbonated magnesium hydroxide (PCMH) is a suitable agent for use in cosmetic deodorant compositions. In one embodiment of the invention, the PCMH was prepared from an aqueous slurry of magnesium hydroxide, which was injected with carbon dioxide under controlled conditions, so that a defined portion of the magnesium hydroxide (MH) reacted to provide magnesium carbonate (MC); the slurry was dried to a moisture level of 2% or less, when measured, for example, as loss on drying at 105° C. for 60 minutes, and the powder was milled. For 10% carbonation for example, the reaction ran according to the following equation:

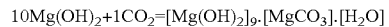

Figure 1:
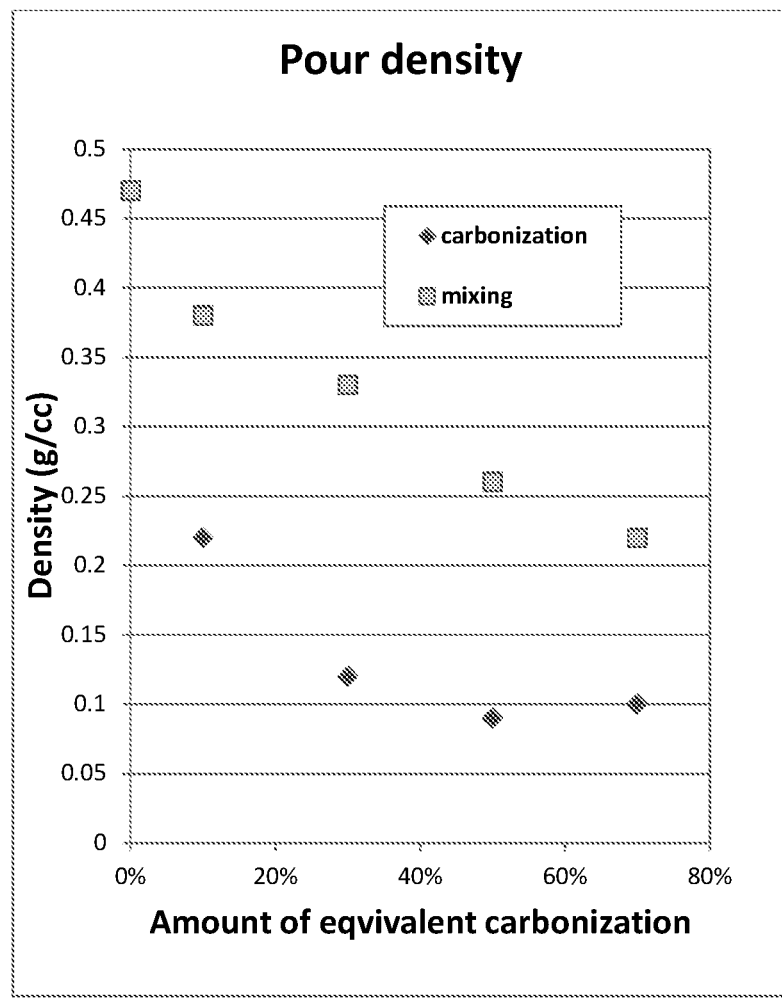
Figure 2:
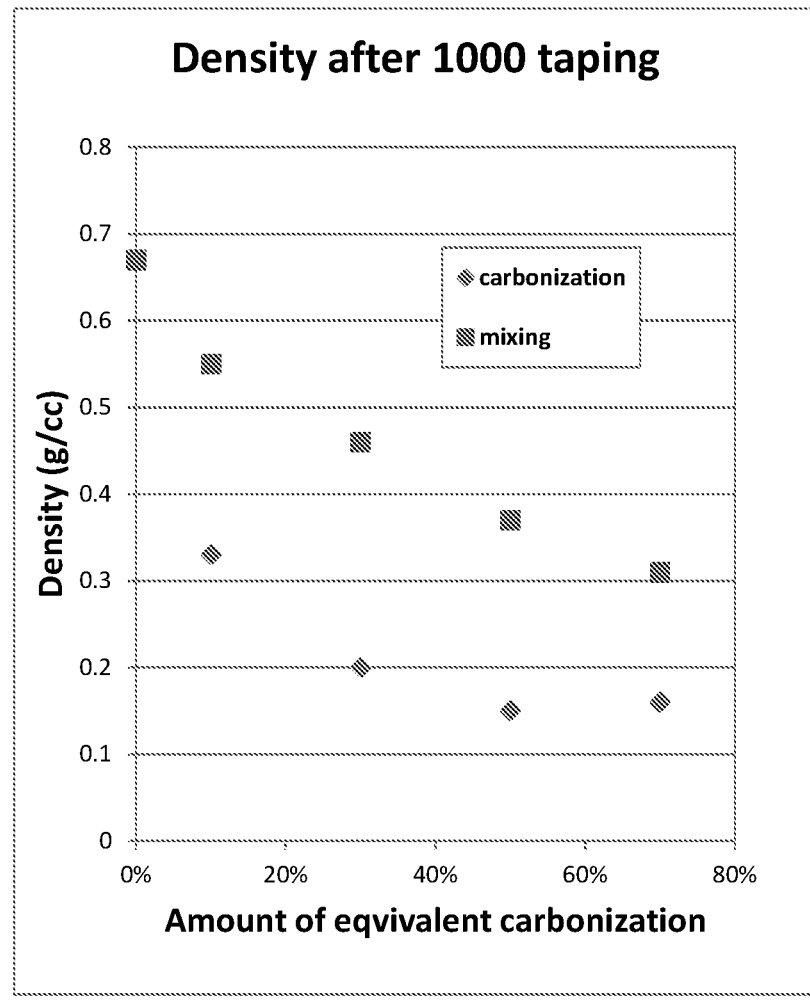
FIG. 2. shows the tapped density measurements for partially carbonized magnesium hydroxide (PCMH) in accordance with the invention (diamonds) and for comparative mixtures of magnesium hydroxide and carbonate (squares)
Figure 3:
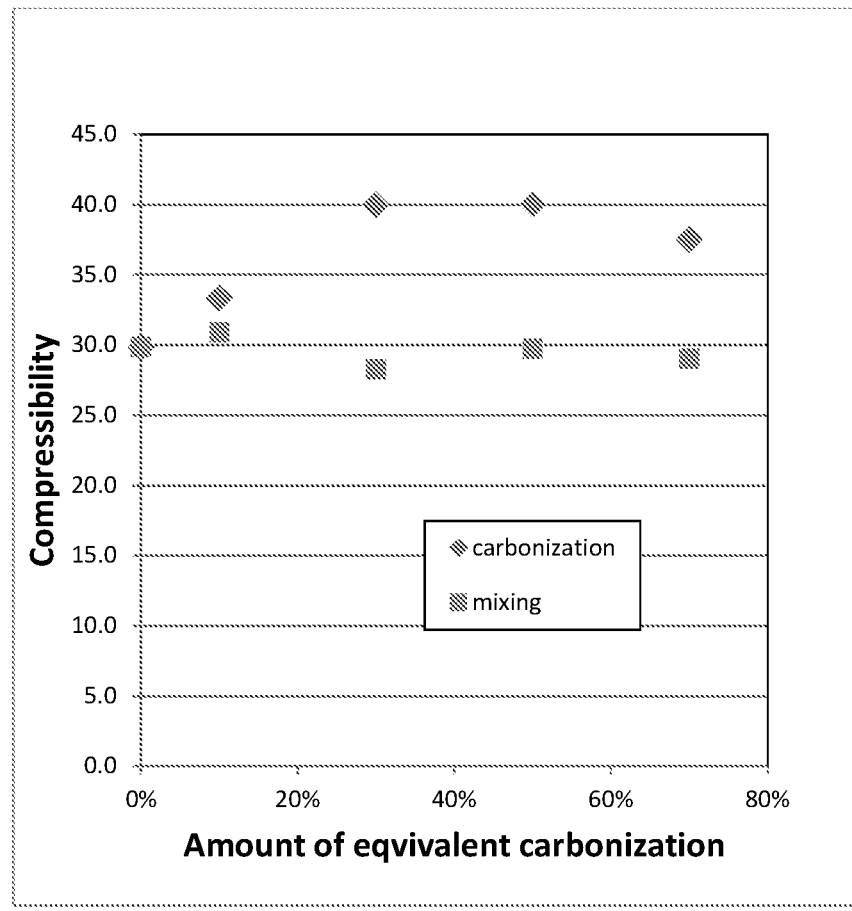
FIG. 3. shows the compressibility values calculated from the bulk densities and tapped densities, as a relative density increase, for partially carbonized magnesium hydroxide (PCMH) in accordance with the invention (diamonds) and for comparative mixtures of magnesium hydroxide and carbonate (squares)

The right side of the equation shows the product which is a homogeneous mixture of magnesium hydroxide (about 83.5 wt %), magnesium carbonate (about 13.5 wt %) and water (about 3 wt %)—constituting a PCMH product. The PCMH products were characterized by several parameters relevant for their use in cosmetic compositions, including their bulk density, tap density, etc. It was found that similar compositions obtained without carbonization, for example by mixing magnesium hydroxide (MH) with magnesium carbonate (MC) or by employing basic magnesium carbonate [BMC=$(MgCO_3)_4 \cdot Mg(OH)_2 \cdot 4H_2O$], differed in their physical properties. For example, a mixture of about 12 wt % BMC and about 88 wt % of MH has an overall composition similar as PCMH shown in the above equation, but it exhibited higher bulk density (pour density) and also higher tapping density, the carbonated magnesium hydroxide being more fluffy than a physical mixture of components, and it kept this feature even after intensive tapping (see FIG. 1 and FIG. 2). Carbonated magnesium hydroxide exhibited higher tapping compressibility (FIG. 3). In various experiments, between 0% and 80% hydroxide was converted to carbonate (the extent of carbonation 0-80%). In a preferred embodiment of the invention, partially carbonated magnesium hydroxide comprising the carbonation extent of between about 5% and about 75%, preferably between about 10% and about 70% is used for preparing cosmetic perspiration-reducing and/or deodorant compositions of the invention. Partially carbonated magnesium hydroxide products comprising the carbonation extent of, for example, about 10% or about 70% are abbreviated here as PCMH10 and PCMH70, respectively.

Figure 4:
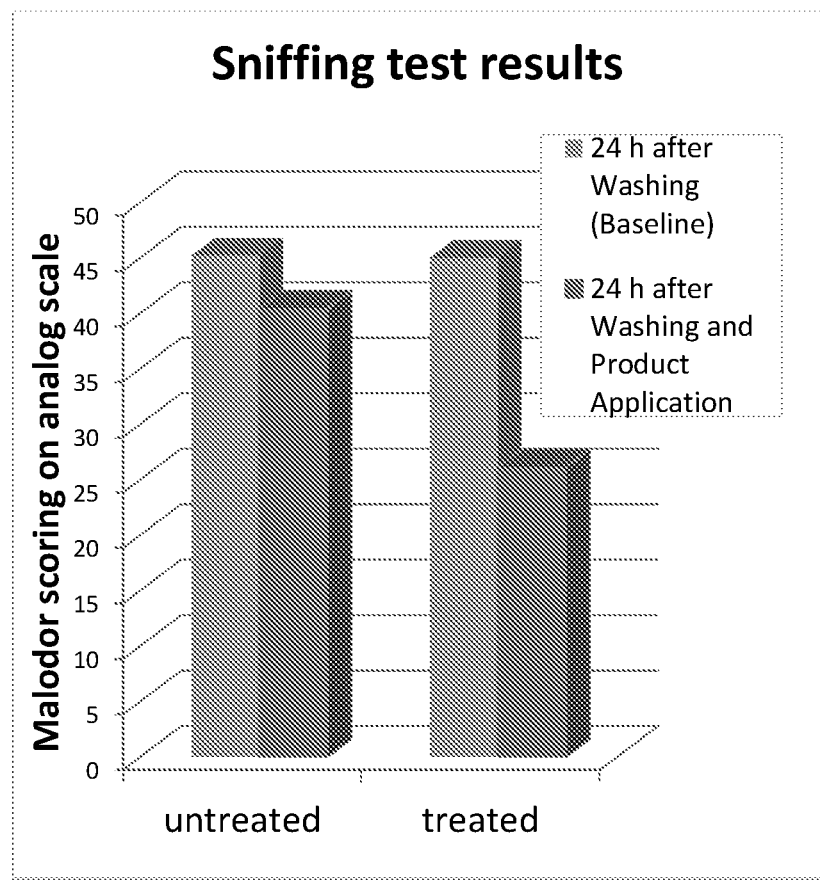
FIG. 4. shows the results of the sniffing test; left for untreated and right for treated group (with the deodorant based on PCMH), the first column being a comparative baseline.
Figure 5:
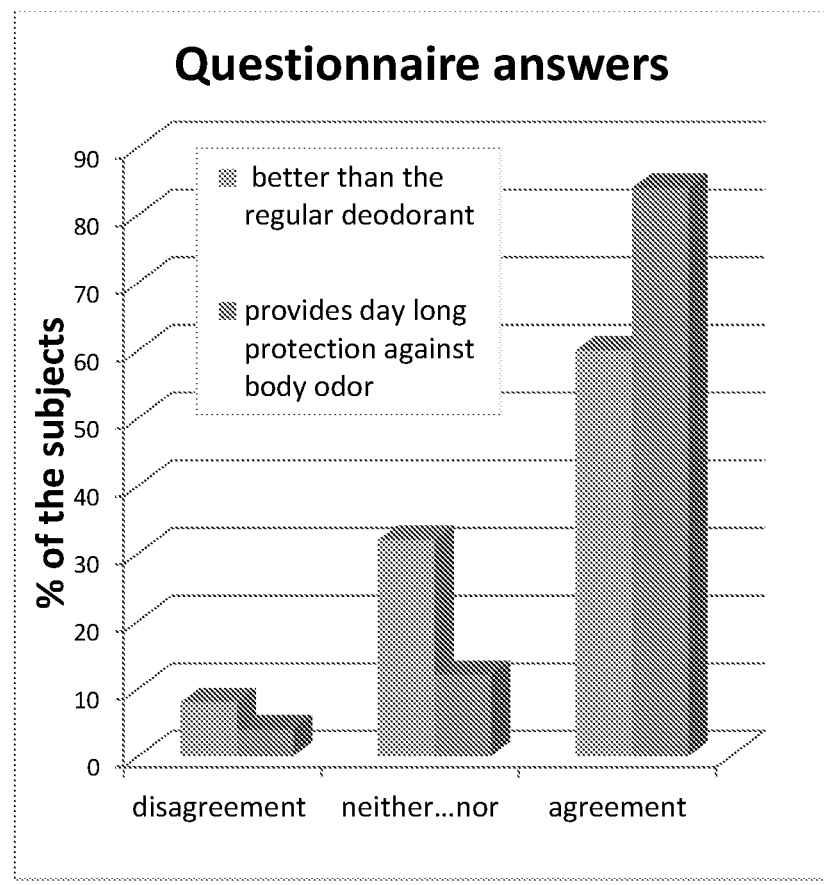
FIG. 5. shows the questionnaire answers.
Figure 6:
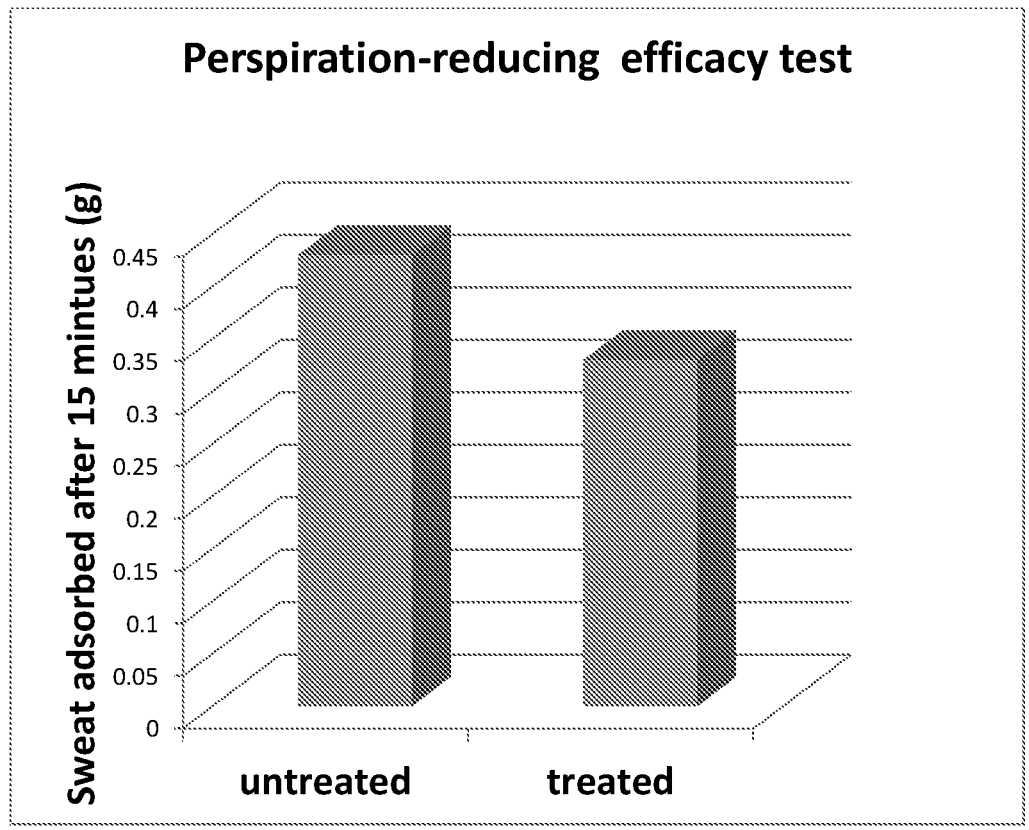
FIG. 6. shows the results of the perspiration-reducing efficacy test on the back.

A cosmetic formulation in accordance with the invention usually comprises between 5 and 25 wt % PCMH, and the rest cosmetically acceptable surfactants and solvents, the formulation being, for example a stick, spray, roll-on, etc. The formulation usually exhibits antimicrobial activity, particularly antibacterial activity; for example, the formulation reduces the concentration of *Staphylococcus* species in vitro. Perspiration-reducing and deodorant formulations in accordance with the invention were prepared and tested; the tests showed a good perspiration-reducing and deodorant activity (FIG. 4, FIG. 5, FIG. 6). In some embodiments, the perspiration-reducing cosmetic formulation of the invention comprising a PCMH composition reduces the sweat formation, as measured by the back perspiration-reducing efficacy test, by at least about 10%, such as by at least 20%. The results of the sniffing test, as well as the questionnaire answers of volunteer users, confirm excellent potential of the PCMH composition for use in reducing perspiration and/or malodors. No irritation or sensitization was noticed in any one of the volunteer subjects. A composition containing PCMH may advantageously serve in safe cosmetic perspiration-reducing or deodorant formulations.

Many perspiration-reducing or deodorant formulations contain at least 15 wt % of aluminum or aluminum-zirconium salts, and often up to 25 wt %. However, the majority of breast cancers occur close to the armpit where deodorants are applied, and aluminum is suspected, among other harmful effects, of being able to cause DNA alterations. A composition containing PCMH in accordance with the invention may substitute for a part of aluminum or aluminum-zirconium salts usually used in perspiration-reducing or deodorant formulations, or it may entirely replace the salts. In one aspect of the invention, the perspiration-reducing or deodorant formulations contain 10 wt % or less of aluminum or zirconium salts, for example less than 9 wt % or less than 8 wt % or less than 7 wt % or less than 6 wt % or less than 5 wt % aluminum or zirconium salts. In one embodiment of the invention, the perspiration-reducing or deodorant formulation contains up to 10 wt % aluminum or zirconium salts, for example up to 7 wt % or up to 6 wt % or up to 5 wt %. In another aspect of the invention, the perspiration-reducing or deodorant formulation is free of aluminum or zirconium salts.

The PCMH product for cosmetic compositions in accordance with the invention preferably comprises partially carbonated magnesium hydroxide, in which carbon dioxide converts from about 5% to about 75% of magnesium hydroxide to magnesium carbonate, preferably from about 10% to about 70%, and more preferably from about 10% to about 50% magnesium hydroxide to magnesium carbonate.

In preferred embodiments, the PCMH product in accordance with the invention comprises between about 20 and 85 wt % magnesium hydroxide, between about 12 and 65 magnesium carbonate, and between 2 and 15 wt % water. The PCMH in accordance with the invention will typically comprise magnesium carbonate (MC) being formed from magnesium hydroxide and carbon dioxide and being dispersed in magnesium hydroxide, MC being in an amount of about 5, about 10, about 20, about 30, about 40, about 50, about 60, or about 70 wt %, based on the total PCMH weight. The PCMH in accordance with the invention will typically comprise water being formed from magnesium hydroxide and carbon dioxide in an amount of about of up to 5, up to 10, or up to 15 wt % based on the total PCMH weight. When employing the term "about" before a value X, intended is the range of X±X/5.

The invention will be further described and illustrated in the following examples.

EXAMPLES

Example 1

Figure 7:
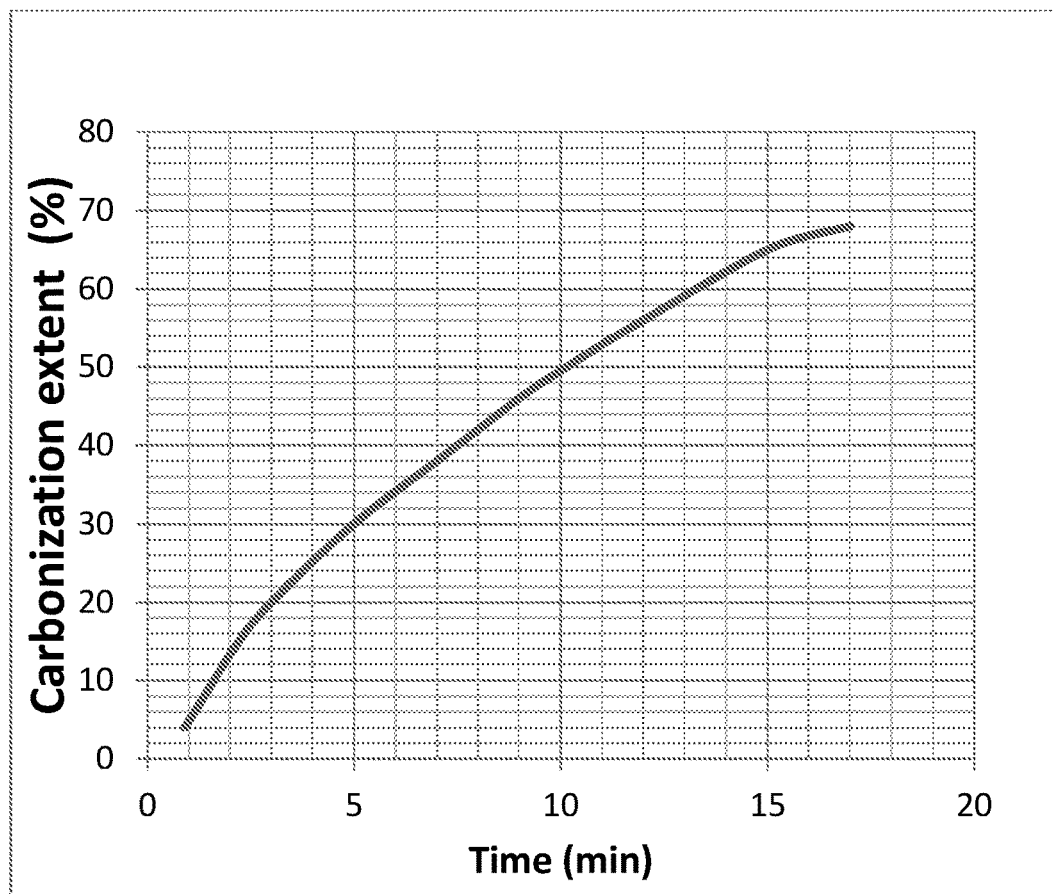
FIG. 7. is the relation between the carbonation time and the carbonation extent (in %) in one experimental arrangement according to the invention.

Partially carbonated magnesium hydroxide (PCMH) according to the invention was prepared, in one embodiment, from MH aqueous slurry, 10-40%, in a mixing tank. The slurry was heated to 30-80° C., and carbon dioxide was injected to the bottom of mixing shaft at an overpressure of 0.3-0.9 bar. The flow rate was adjusted, so that bubbles of gas appear on the mixture surface (excess of carbon dioxide). After certain reaction time, according to required carbonation extent, the process is stopped. The slurry was filtered and dried either in spray dryer or by another type of drying technology where exhausted gas temp is not less than 130-160° C. The moisture level of the dried material was less than 2%, when measured as loss of drying at 105° C. for 60 minutes. The dry powder was milled, and its content of magnesium hydroxide and water was determined, employing thermogravimetric analysis. The reaction time for a desired carbonation extent was assessed from a calibration curve, reaction time versus achieved carbonization, found for the relevant reaction arrangement. A calibration curve for a specific arrangement is shown in FIG. 7.

Example 2

Comparative samples comprising magnesium hydroxide and magnesium carbonate of various ratios were prepared. In one series of experiments, basic magnesium carbonate $[(MgCO3)_4.Mg(OH)_2.4H2O]$ was mixed with magnesium hydroxide, whereby simulating compositions obtained in accordance with the invention and having the same hydroxide/carbonate/water ratios.

The content of free water was determined by loss on drying at 105° C. for 60 minutes. The content of bound water was determined by loss of drying at 180° C. for 30 minutes. The bulk density and tapped density were measured by pouring 50 g of powder into a volumetric cylinder; the bulk volume in ml was read immediately after pouring ($V_0$), followed by 1000 tapping using a pharma test instrument and repeated reading of the volume ($V_{1000}$). The bulk density and the tapped density were calculated (50/V). Compressibility was calculated: $100*(1-V_{1000}/V_0)$.

Figure 8A:
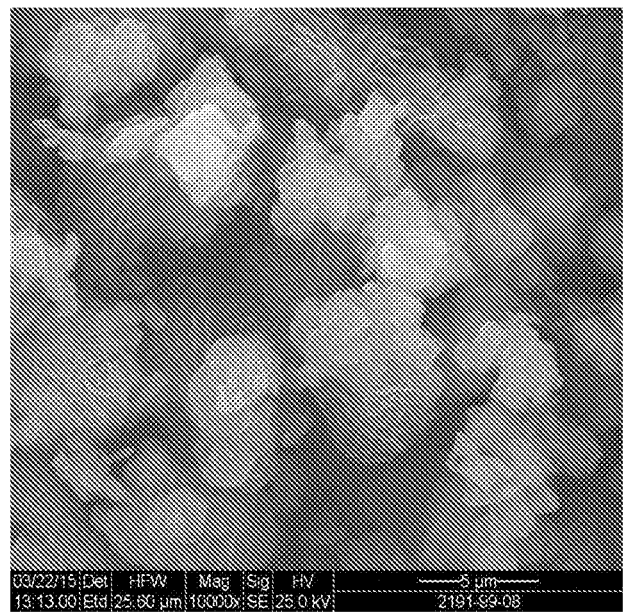
FIG. 8. shows SEM images, 10000 magnification, the abscissa corresponding to 5 μm, of a PCMH10 sample according to the invention and a comparative example; 8A shows PCMH, 10% carbonization, according to the invention; 8B shows an artificial mixture of magnesium hydroxide and basic magnesium hydroxide tetrahydrate simulating 10% carbonization.
Figure 8B:
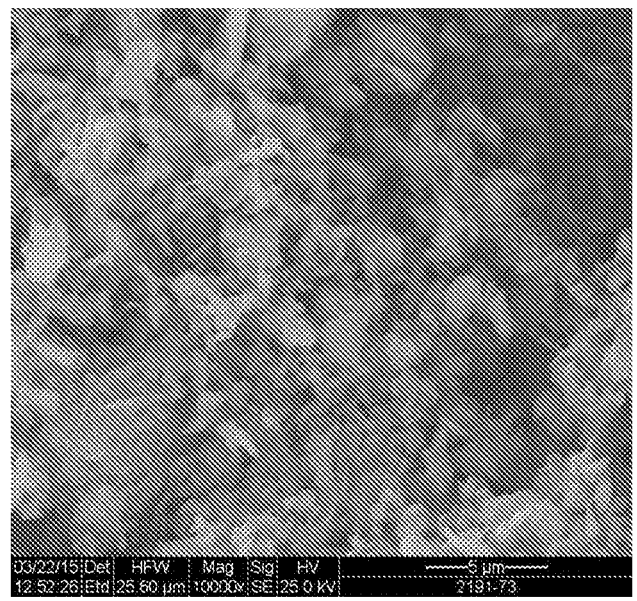

Both types of materials, partially carbonated magnesium hydroxide in accordance with the invention and the simulating physical mixtures, were further characterized (not shown) by measuring nitrogen adsorption/desorption on the powders, BET, total pore volumes, average pore diameters, particle size distributions, XRD patterns and TGA profiles. The two types of powders, even though having similar chemical compositions, exhibited different physical properties (see, for example, the compressibility differences in FIG. 3) and micro-structure features (see, for example, SEM images in FIG. 8).

Experiment 3

Deodorant formulations in accordance with the invention were prepared by mixing PCMH10 prepared according to the invention with cosmetically acceptable components according to the following tables:

| Component | wt % |
|---|---|
| 20% PCMH roll-on | |
| Water | 58.62 |
| xanthan gum | 0.08 |
| steareth-2 | 2.00 |
| steareth-21 | 1.00 |
| PPG 15-stearylether | 3.00 |
| fumed silica | 0.50 |
| cyclopentasiloxane | 10.00 |
| C12-15 alkylbenzoate | 3.00 |
| PCMH10 | 20.00 |
| phenoxyethanol + ethylhexylglycerin | 0.80 |
| Perfume | 1.00 |
| 20% PCMH stick | |
| cyclopentasiloxane | 38.45 |
| phenyltrimethicone | 2.00 |

-continued

| Component | wt % |
| --- | --- |
| C12-15 alkylbenzoate | 14.00 |
| Petrolatum | 1.50 |
| Stearylalcohol | 19.00 |
| Trihydroxystearin | 2.00 |
| talc | 1.00 |
| PCMH10 | 20.00 |
| BHT | 0.05 |
| Perfume | 2.00 |

| Component | wt % |
| --- | --- |
| 25% PCMH spray | |
| cyclopentasiloxane | 42.10 |
| phenyltrimethicone | 5.00 |
| C12-15 alkylbenzoate | 15.00 |
| Bisabolol | 0.20 |
| Farnesol | 0.30 |
| ethylhexylglycerin | 0.30 |
| stearalkonium hectorite + propylene carbonate + caprylic/capric triglyceride | 6.00 |
| PCMH10 | 25.00 |
| BHT | 0.10 |
| Perfume | 6.00 |
| Liquid/gas | 15/85 |
| 10% PCMH + 10% Al/Zr roll-on | |
| water | 40.05 |
| xanthan gum | 0.08 |
| steareth-2 | 2.00 |
| steareth-21 | 1.00 |
| PPG 15-stearyl ether | 3.00 |
| fumed silica | 0.50 |
| cyclopentasiloxane | 10.00 |
| C12-15 alkyl benzoate | 3.00 |
| PCMH10 | 10.00 |
| aluminum zirconium tetrachlorhydrex GLY-35% aq. solution | 28.57 |
| phenoxyethanol + ethylhexyl glycerin | 0.80 |
| perfume | 1.00 |

Experiment 4

Sniff test was performed in Institute for Applied Dermatological Research, pro-DERM Hamburg, Germany, in June 2015, by experts (sniffers) trained for evaluating the efficacy of cosmetic products against axillary malodor. Twenty five subjects used the roll-on deodorant according to the invention. According to the results of the study, a significant difference in sweat odor rating was documented between the test product and the untreated control 24 hours after product application in favor of the test product (FIG. 4). The subjects filled in a questionnaire and expressed their subjective experience, mostly positive (FIG. 5); the subjects notices no sticky feel or unpleasant residues on the skin, no stains on clothes, and found the test product easy to spread.

Experiment 5

Sensitizing properties of the roll-on deodorant according to the invention, was examined in the The Institute for Skin Reseach, Tel Aviv, Israel, on 50 volunteers. The hypoallergic test showed no allergic reaction for the deodorant of the invention.

Experiment 6

Perspiration-reducing efficacy of the roll-on deodorant according to the invention was measured in the The Institute for Skin Research, Tel Aviv, Israel, on 10 volunteers. Gravimetrical assessment of the sweat quantity on the back of the subjects showed a reduction of 23% (FIG. 6).

Experiment 7

Odor-reducing efficacy of the roll-on deodorant according to the invention, comprising 20% PCMH (as described in Example 3) was compared with a roll-on aluminum based deodorant containing 20% active material based on aluminum with otherwise same components. Six subjects (4 males, 2 females) used both deodorants in two armpits in parallel. Sniffers assessed both armpits every three hours from the time 0 to the time 24 hours, and scored the odor from 1 to 5, wherein 1 is no odor, 2 is weak, 3 is medium, 4 is strong, and 5 very strong. The average score for Al-based roll-on was 1.2 and for PCMH roll-on was 1.4.

Experiment 8

The antimicrobial activity of formulation "20% PCMH roll-on" as described in Example 3 was assessed according to a time-kill procedure ASTM E2315-03 in the Institute for Food Microbiology and Consumer Goods Ltd., Nesher, Israel. Two medically relevant types of bacteria which are a part of human skin flora, *Staphylococcus epidermidis* and *Staphylococcus aureus*, were exposed for two hours to the formulation and the reduction of their concentration was measured. As for *S. epidermidis*, formulation 20% PCMH roll-on according to the invention reduced its concentration by 99%, as for *S. aureus*, it could not be detected.

While the invention has been described using some specific examples, many modifications and variations are possible. It is therefore understood that the invention is not intended to be limited in any way, other than by the scope of the appended claims.

The invention claimed is:

1. A cosmetic formulation comprising a partially carbonated magnesium hydroxide (PCMH) of formula (1):

$$[Mg(OH)_2]_{10-x} \cdot [MgCO_3]_x \cdot [H_2O]_x \tag{1}$$

wherein x is a real number between about 1 and 7.

2. The cosmetic formulation according to claim 1 being perspiration-reducing formulation or deodorant formulation.

3. The cosmetic perspiration-reducing or deodorant formulation according to claim 2, comprising PCMH in an amount of from 5 to 30 wt %.

4. The cosmetic perspiration-reducing or deodorant formulation according to claim 2, wherein said PCMH consists of 20 to 85 wt % magnesium hydroxide, 12 to 65 magnesium carbonate, and 2 to 15 wt % water.

5. The cosmetic perspiration-reducing or deodorant formulation according to claim 2, comprising up to 10 wt % aluminum or zirconium salts.

6. The cosmetic perspiration-reducing or deodorant formulation according to claim 2, lacking aluminum or zirconium salts.

7. The cosmetic perspiration-reducing or deodorant formulation according to claim 2, comprising said partially carbonated magnesium hydroxide with solvents and optionally with additional components selected from surfactants, bulking agents, and fragrance components, said formulation exhibiting antimicrobial activity.

8. A dermatologically safe agent for use in cosmetic formulations, essentially consisting of a partially carbonated magnesium hydroxide (PCMH) of formula (1):

$$[Mg(OH)_2]_{10-x} \cdot [MgCO_3]_x \cdot [H_2O]_x \tag{1}$$

wherein x is a real number between about 1 and 7.

9. The dermatologically safe agent according to claim 8 being cosmetically active agent or perspiration-reducing agent or deodorant agent.

10. A method for reducing the amount of aluminum-based salts in deodorants and perspiration-reducing formulations or for replacing said salts, comprising
  i) providing cosmetically acceptable magnesium hydroxide and partially reacting it with carbon dioxide, wherein converting between about 10 and 70% of said hydroxide to carbonate, to provide a partially carbonated magnesium hydroxide (PCMH) essentially consisting of magnesium carbonate and water homogeneously dispersed in magnesium hydroxide;
  ii) mixing said PCMH with cosmetically acceptable solvents and/or surfactants, and optionally with additional components selected from surfactants, emollients, buffers, bulking agents, thickening agents, moisturizers, fragrance components, and preservatives, thereby obtaining a deodorant or perspiration-reducing formulation free of aluminum and zirconium salts, wherein said PCMH constitutes between 5 and 25 wt % of the formulation; and optionally
  iii) admixing to said formulation of step ii) up to 10 wt % of aluminum or zirconium salts, based on the weight of said formulation.

11. A method of manufacturing a cosmetic deodorant or perspiration-reducing formulation comprising steps of:
  i) providing cosmetically acceptable magnesium hydroxide and partially reacting it with carbon dioxide, wherein converting between about 10 and 70% of said hydroxide to carbonate, to provide a partially carbonated magnesium hydroxide (PCMH) essentially consisting of magnesium carbonate and water homogeneously dispersed in magnesium hydroxide;
  ii) mixing said PCMH with cosmetically acceptable solvents and/or surfactants; and optionally
  iii) mixing with additional components selected from emollients, buffers, bulking agents, thickening agents, moisturizers, fragrance components, and preservatives;
thereby obtaining a safe deodorant or perspiration-reducing formulation, free of aluminum and zirconium salts.

12. The method of claim 11, comprising steps of
  (i) preparing an aqueous 10-40% slurry of magnesium hydroxide in a reactor;
  (ii) heating the slurry to 30-80° C. and stirring;
  (iii) injecting to the bottom of the reactor carbon dioxide for the time needed to the desired carbonation; and
  (iv) removing the partially carbonated magnesium hydroxide from the slurry and drying it to a moisture level of less than 2%, when measured as loss of drying at 105° C. for 60 minutes.

\* \* \* \* \*